United States Patent
Jafari et al.

(10) Patent No.: US 8,746,248 B2
(45) Date of Patent: Jun. 10, 2014

(54) DETERMINATION OF PATIENT CIRCUIT DISCONNECT IN LEAK-COMPENSATED VENTILATORY SUPPORT

(75) Inventors: Mehdi M. Jafari, Laguna Hills, CA (US); Rhomere S. Jimenez, Winchester, CA (US); Gail F. Upham, Fallbrook, CA (US)

(73) Assignee: Covidien LP, Mansfield, MA (US)

( * ) Notice: Subject to any disclaimer, the term of this patent is extended or adjusted under 35 U.S.C. 154(b) by 714 days.

(21) Appl. No.: 12/334,354

(22) Filed: Dec. 12, 2008

(65) Prior Publication Data

US 2010/0147303 A1 Jun. 17, 2010

(51) Int. Cl.
*A61M 16/00* (2006.01)

(52) U.S. Cl.
CPC .................... *A61M 16/0051* (2013.01)
USPC ............. 128/204.23; 128/204.21; 128/204.18

(58) Field of Classification Search
CPC ................. A61M 16/0051; A61M 2016/0021; A61M 2205/15; A61M 2013/0036; A61M 2016/0069; A61M 2016/204; A61M 16/00; A61M 2016/0039; A61M 16/0066; A61M 16/06; A61M 16/205; A61M 2205/3561; A61M 2230/04; A61M 2016/0027; A61M 2205/50; A61M 1/16; A61M 2016/0015; A61M 2016/003
USPC ............. 128/204.23, 204.21, 204.18, 205.11, 128/205.17, 203.12, 200.24, 202.22, 128/204.26, 205.25, 207.18, 848
See application file for complete search history.

(56) References Cited

U.S. PATENT DOCUMENTS

| | | | |
|---|---|---|---|
| 3,805,780 A | 4/1974 | Cramer et al. | |
| 3,941,124 A | 3/1976 | Rodewald et al. | |
| 4,056,098 A | 11/1977 | Michel et al. | |
| 4,305,388 A | 12/1981 | Brisson | |
| 4,340,044 A | 7/1982 | Levy et al. | |
| 4,448,192 A | 5/1984 | Stawitcke et al. | |
| 4,752,089 A | 6/1988 | Carter | |
| 4,766,894 A * | 8/1988 | Legrand et al. | 128/204.21 |
| 4,921,642 A | 5/1990 | LaTorraca | |

(Continued)

FOREIGN PATENT DOCUMENTS

DE 19808543 A1 11/1998
EP 0425092 A 5/1991

(Continued)

OTHER PUBLICATIONS

PCT International Search Report and Written Opinion in Application PCT/US201/0026618, mailed Jun. 22, 2010, 19 pgs.

(Continued)

*Primary Examiner* — Annette Dixon
(74) *Attorney, Agent, or Firm* — Merchant & Gould P.C.

(57) ABSTRACT

This disclosure describes systems and methods for detecting disconnect conditions in a ventilator. The disclosure describes a model-based enhancement to conventional disconnect detection. The methods and systems described herein compensate for the additional leakage that occurs due to inelastic and elastic leaks in the ventilation system. One method described includes calculating the actual leakage from the ventilation system including leaks from elastic leakage and inelastic leakage based on measurements of pressure and flow in the ventilation system for a breath and then comparing this leakage to a calculated hypothetical maximum allowable leakage determined based on an operator-selected maximum allowable leakage and the measurements of pressure for the same breath. Disconnection is assumed if the actual leakage is greater than the maximum allowable leakage.

15 Claims, 4 Drawing Sheets

(56) References Cited

U.S. PATENT DOCUMENTS

| | | | |
|---|---|---|---|
| 4,939,647 | A | 7/1990 | Clough et al. |
| 4,954,799 | A | 9/1990 | Kumar |
| 4,971,052 | A | 11/1990 | Edwards |
| 4,972,842 | A * | 11/1990 | Korten et al. ............ 600/529 |
| 4,986,268 | A | 1/1991 | Tehrani |
| 5,057,822 | A | 10/1991 | Hoffman |
| 5,065,350 | A | 11/1991 | Fedder |
| 5,072,728 | A | 12/1991 | Pasternack |
| 5,072,737 | A | 12/1991 | Goulding |
| 5,094,235 | A | 3/1992 | Westenskow et al. |
| 5,148,802 | A | 9/1992 | Sanders et al. |
| 5,150,291 | A | 9/1992 | Cummings et al. |
| 5,161,525 | A | 11/1992 | Kimm et al. |
| 5,237,987 | A | 8/1993 | Anderson et al. |
| 5,239,995 | A | 8/1993 | Estes et al. |
| 5,259,373 | A * | 11/1993 | Gruenke et al. ......... 128/204.23 |
| 5,271,389 | A | 12/1993 | Isaza et al. |
| 5,279,549 | A | 1/1994 | Ranford |
| 5,299,568 | A | 4/1994 | Forare et al. |
| 5,301,921 | A | 4/1994 | Kumar |
| 5,313,937 | A | 5/1994 | Zdrojkowski et al. |
| 5,315,989 | A | 5/1994 | Tobia |
| 5,316,009 | A * | 5/1994 | Yamada .................... 600/533 |
| 5,319,540 | A | 6/1994 | Isaza et al. |
| 5,325,861 | A | 7/1994 | Goulding |
| 5,333,606 | A | 8/1994 | Schneider et al. |
| 5,339,807 | A | 8/1994 | Carter |
| 5,343,857 | A | 9/1994 | Schneider et al. |
| 5,351,522 | A | 10/1994 | Lura |
| 5,357,946 | A | 10/1994 | Kee et al. |
| 5,365,922 | A | 11/1994 | Raemer |
| 5,368,019 | A | 11/1994 | LaTorraca |
| 5,383,449 | A | 1/1995 | Forare et al. |
| 5,385,142 | A | 1/1995 | Brady et al. |
| 5,388,575 | A | 2/1995 | Taube |
| 5,390,666 | A | 2/1995 | Kimm et al. |
| 5,398,682 | A | 3/1995 | Lynn |
| 5,401,135 | A | 3/1995 | Stoen et al. |
| 5,402,796 | A | 4/1995 | Packer et al. |
| 5,407,174 | A | 4/1995 | Kumar |
| 5,413,110 | A | 5/1995 | Cummings et al. |
| 5,429,123 | A | 7/1995 | Shaffer et al. |
| 5,433,193 | A | 7/1995 | Sanders et al. |
| 5,438,980 | A | 8/1995 | Phillips |
| 5,443,075 | A | 8/1995 | Holscher |
| 5,492,113 | A | 2/1996 | Estes et al. |
| 5,503,146 | A | 4/1996 | Froehlich et al. |
| 5,503,147 | A | 4/1996 | Bertheau |
| 5,513,631 | A | 5/1996 | McWilliams |
| 5,517,983 | A | 5/1996 | Deighan et al. |
| 5,520,071 | A | 5/1996 | Jones |
| 5,524,615 | A | 6/1996 | Power |
| 5,531,221 | A | 7/1996 | Power |
| 5,535,738 | A | 7/1996 | Estes et al. |
| 5,540,220 | A | 7/1996 | Gropper et al. |
| 5,542,415 | A | 8/1996 | Brody |
| 5,544,674 | A | 8/1996 | Kelly |
| 5,549,106 | A | 8/1996 | Gruenke et al. |
| 5,551,418 | A | 9/1996 | Estes et al. |
| 5,551,419 | A | 9/1996 | Froehlich et al. |
| 5,555,880 | A | 9/1996 | Winter et al. |
| 5,596,984 | A | 1/1997 | O'Mahony et al. |
| 5,598,838 | A | 2/1997 | Servidio et al. |
| 5,605,151 | A | 2/1997 | Lynn |
| 5,623,923 | A | 4/1997 | Bertheau et al. |
| 5,630,411 | A | 5/1997 | Holscher |
| 5,632,269 | A | 5/1997 | Zdrojkowski |
| 5,632,270 | A | 5/1997 | O'Mahony et al. |
| 5,645,048 | A | 7/1997 | Brodsky et al. |
| 5,645,053 | A | 7/1997 | Remmers et al. |
| 5,660,171 | A | 8/1997 | Kimm et al. |
| 5,664,560 | A | 9/1997 | Merrick et al. |
| 5,664,562 | A | 9/1997 | Bourdon |
| 5,671,767 | A | 9/1997 | Kelly |
| 5,672,041 | A | 9/1997 | Ringdahl et al. |
| 5,673,689 | A | 10/1997 | Power |
| 5,685,296 | A | 11/1997 | Zdrojkowski et al. |
| 5,687,715 | A | 11/1997 | Landis et al. |
| 5,692,497 | A | 12/1997 | Schnitzer et al. |
| 5,715,812 | A | 2/1998 | Deighan et al. |
| 5,752,509 | A | 5/1998 | Lachmann et al. |
| 5,762,480 | A | 6/1998 | Adahan |
| 5,771,884 | A | 6/1998 | Yarnall et al. |
| 5,791,339 | A | 8/1998 | Winter |
| 5,794,615 | A | 8/1998 | Estes |
| 5,794,986 | A | 8/1998 | Gansel et al. |
| 5,803,065 | A | 9/1998 | Zdrojkowski et al. |
| 5,813,399 | A | 9/1998 | Isaza et al. |
| 5,823,187 | A | 10/1998 | Estes et al. |
| 5,826,575 | A | 10/1998 | Lall |
| 5,829,441 | A | 11/1998 | Kidd et al. |
| 5,864,938 | A | 2/1999 | Gansel et al. |
| 5,865,168 | A | 2/1999 | Isaza |
| 5,876,352 | A | 3/1999 | Weismann |
| 5,881,717 | A | 3/1999 | Isaza |
| 5,881,723 | A | 3/1999 | Wallace et al. |
| 5,884,622 | A | 3/1999 | Younes |
| 5,884,623 | A | 3/1999 | Winter |
| 5,891,023 | A | 4/1999 | Lynn |
| 5,901,704 | A | 5/1999 | Estes et al. |
| 5,904,141 | A | 5/1999 | Estes et al. |
| 5,909,731 | A | 6/1999 | O'Mahony et al. |
| 5,915,379 | A | 6/1999 | Wallace et al. |
| 5,915,380 | A | 6/1999 | Wallace et al. |
| 5,915,382 | A | 6/1999 | Power |
| 5,918,597 | A | 7/1999 | Jones et al. |
| 5,921,238 | A | 7/1999 | Bourdon |
| 5,921,920 | A | 7/1999 | Marshall et al. |
| 5,927,274 | A | 7/1999 | Servidio et al. |
| 5,934,274 | A | 8/1999 | Merrick et al. |
| 5,970,975 | A | 10/1999 | Estes et al. |
| 6,024,089 | A | 2/2000 | Wallace et al. |
| 6,029,664 | A | 2/2000 | Zdrojkowski et al. |
| 6,041,780 | A | 3/2000 | Richard et al. |
| 6,047,860 | A | 4/2000 | Sanders |
| 6,055,981 | A | 5/2000 | Laswick et al. |
| 6,059,732 | A | 5/2000 | Orr et al. |
| 6,076,523 | A | 6/2000 | Jones et al. |
| 6,105,575 | A | 8/2000 | Estes et al. |
| 6,116,240 | A | 9/2000 | Merrick et al. |
| 6,116,464 | A | 9/2000 | Sanders |
| 6,123,073 | A | 9/2000 | Schlawin et al. |
| 6,123,074 | A | 9/2000 | Hete et al. |
| 6,135,106 | A | 10/2000 | Dirks et al. |
| 6,142,150 | A | 11/2000 | O'Mahoney et al. |
| 6,148,814 | A | 11/2000 | Clemmer et al. |
| 6,152,129 | A | 11/2000 | Berthon-Jones |
| 6,158,432 | A | 12/2000 | Biondi et al. |
| 6,161,539 | A | 12/2000 | Winter |
| 6,220,245 | B1 | 4/2001 | Takabayashi et al. |
| 6,223,064 | B1 | 4/2001 | Lynn et al. |
| 6,253,765 | B1 | 7/2001 | Högnelid et al. |
| 6,257,234 | B1 | 7/2001 | Sun |
| 6,269,812 | B1 | 8/2001 | Wallace et al. |
| 6,273,444 | B1 | 8/2001 | Power |
| 6,279,569 | B1 | 8/2001 | Berthon-Jones |
| 6,283,119 | B1 | 9/2001 | Bourdon |
| 6,286,508 | B1 | 9/2001 | Remmers et al. |
| 6,305,372 | B1 | 10/2001 | Servidio |
| 6,305,373 | B1 | 10/2001 | Wallace et al. |
| 6,305,374 | B1 | 10/2001 | Zdrojkowski et al. |
| 6,321,748 | B1 | 11/2001 | O'Mahony |
| 6,325,785 | B1 | 12/2001 | Babkes et al. |
| 6,342,039 | B1 | 1/2002 | Lynn et al. |
| 6,357,438 | B1 | 3/2002 | Hansen |
| 6,360,741 | B2 | 3/2002 | Truschel |
| 6,360,745 | B1 | 3/2002 | Wallace et al. |
| 6,369,838 | B1 | 4/2002 | Wallace et al. |
| 6,371,114 | B1 | 4/2002 | Schmidt et al. |
| 6,390,091 | B1 | 5/2002 | Banner et al. |
| 6,412,483 | B1 | 7/2002 | Jones et al. |
| 6,425,395 | B1 | 7/2002 | Brewer et al. |
| 6,427,689 | B1 | 8/2002 | Estes et al. |
| 6,439,229 | B1 | 8/2002 | Du et al. |

(56) References Cited

U.S. PATENT DOCUMENTS

| | | |
|---|---|---|
| 6,467,478 B1 | 10/2002 | Merrick et al. |
| 6,484,719 B1 | 11/2002 | Berthon-Jones |
| 6,512,938 B2 | 1/2003 | Claure et al. |
| 6,532,957 B2 | 3/2003 | Berthon-Jones |
| 6,532,958 B1 | 3/2003 | Buan et al. |
| 6,532,959 B1 | 3/2003 | Berthon-Jones |
| 6,532,960 B1 | 3/2003 | Yurko |
| 6,536,429 B1 | 3/2003 | Pavlov et al. |
| 6,536,432 B2 | 3/2003 | Truschel |
| 6,539,940 B2 | 4/2003 | Zdrojkowski et al. |
| 6,543,449 B1 | 4/2003 | Woodring et al. |
| 6,546,930 B1 | 4/2003 | Emerson et al. |
| 6,550,478 B2 | 4/2003 | Remmers et al. |
| 6,553,991 B1 | 4/2003 | Isaza |
| 6,553,992 B1 | 4/2003 | Berthon-Jones et al. |
| 6,557,553 B1 | 5/2003 | Borrello |
| 6,561,187 B2 | 5/2003 | Schmidt et al. |
| 6,571,795 B2 | 6/2003 | Bourdon |
| 6,575,163 B1 | 6/2003 | Berthon-Jones |
| 6,578,575 B1 | 6/2003 | Jonson |
| 6,609,016 B1 | 8/2003 | Lynn |
| 6,609,517 B1 | 8/2003 | Estes et al. |
| 6,615,834 B2 | 9/2003 | Gradon et al. |
| 6,622,726 B1 | 9/2003 | Du |
| 6,626,175 B2 | 9/2003 | Jafari et al. |
| 6,629,527 B1 | 10/2003 | Estes et al. |
| 6,640,806 B2 | 11/2003 | Yurko |
| 6,644,310 B1 | 11/2003 | Delache et al. |
| 6,644,312 B2 | 11/2003 | Berthon-Jones et al. |
| 6,644,316 B2 | 11/2003 | Bowman et al. |
| 6,659,101 B2 | 12/2003 | Berthon-Jones |
| 6,668,824 B1 | 12/2003 | Isaza et al. |
| 6,671,529 B2 | 12/2003 | Claure et al. |
| 6,675,801 B2 | 1/2004 | Wallace et al. |
| 6,688,307 B2 | 2/2004 | Berthon-Jones |
| 6,701,926 B2 | 3/2004 | Olsen et al. |
| 6,718,974 B1 | 4/2004 | Moberg |
| 6,722,365 B2 | 4/2004 | Nilsson et al. |
| 6,723,055 B2 | 4/2004 | Hoffman |
| 6,723,132 B2 | 4/2004 | Salehpoor |
| 6,725,447 B1 | 4/2004 | Gilman et al. |
| 6,739,337 B2 | 5/2004 | Isaza |
| 6,748,252 B2 | 6/2004 | Lynn et al. |
| 6,752,150 B1 | 6/2004 | Remmers et al. |
| 6,752,151 B2 | 6/2004 | Hill |
| 6,755,193 B2 | 6/2004 | Berthon-Jones et al. |
| 6,758,216 B1 | 7/2004 | Berthon-Jones et al. |
| 6,760,608 B2 | 7/2004 | Lynn |
| 6,761,165 B2 | 7/2004 | Strickland, Jr. |
| 6,761,167 B2 | 7/2004 | Nadjafizadeh et al. |
| 6,761,168 B1 | 7/2004 | Nadjafizadeh et al. |
| 6,789,541 B2 | 9/2004 | Olsen et al. |
| 6,796,305 B1 | 9/2004 | Banner et al. |
| 6,810,876 B2 | 11/2004 | Berthon-Jones |
| 6,814,074 B1 | 11/2004 | Nadjafizadeh et al. |
| 6,820,613 B2 | 11/2004 | Wenkebach et al. |
| 6,820,618 B2 | 11/2004 | Banner et al. |
| 6,823,866 B2 | 11/2004 | Jafari et al. |
| 6,837,242 B2 | 1/2005 | Younes |
| 6,843,250 B2 | 1/2005 | Efrati |
| 6,866,040 B1 | 3/2005 | Bourdon |
| 6,868,346 B2 | 3/2005 | Larson et al. |
| 6,874,503 B2 | 4/2005 | Rydgren |
| 6,910,480 B1 | 6/2005 | Berthon-Jones |
| 6,910,481 B2 | 6/2005 | Kimmel et al. |
| 6,920,875 B1 | 7/2005 | Hill et al. |
| 6,920,877 B2 | 7/2005 | Remmers et al. |
| 6,932,084 B2 | 8/2005 | Estes et al. |
| 6,945,248 B2 | 9/2005 | Berthon-Jones |
| 6,948,497 B2 | 9/2005 | Zdrojkowski et al. |
| 6,960,854 B2 | 11/2005 | Nadjafizadeh et al. |
| 6,962,155 B1 | 11/2005 | Sinderby |
| 6,986,347 B2 | 1/2006 | Hickle |
| 7,000,612 B2 | 2/2006 | Jafari et al. |
| 7,008,380 B1 | 3/2006 | Rees et al. |
| 7,013,892 B2 | 3/2006 | Estes et al. |
| 7,017,576 B2 | 3/2006 | Olsen et al. |
| 7,036,504 B2 | 5/2006 | Wallace et al. |
| 7,040,320 B2 | 5/2006 | Fjeld et al. |
| 7,044,129 B1 | 5/2006 | Truschel et al. |
| 7,055,522 B2 | 6/2006 | Berthon-Jones |
| 7,066,173 B2 | 6/2006 | Banner et al. |
| 7,073,501 B2 | 7/2006 | Remmers et al. |
| 7,077,131 B2 | 7/2006 | Hansen |
| 7,081,095 B2 | 7/2006 | Lynn et al. |
| RE39,225 E | 8/2006 | Isaza et al. |
| 7,089,936 B2 | 8/2006 | Madaus et al. |
| 7,092,757 B2 | 8/2006 | Larson et al. |
| 7,100,607 B2 | 9/2006 | Zdrojkowski et al. |
| 7,100,608 B2 | 9/2006 | Brewer et al. |
| 7,100,609 B2 | 9/2006 | Berthon-Jones et al. |
| 7,107,991 B2 | 9/2006 | Kolobow |
| 7,117,438 B2 | 10/2006 | Wallace et al. |
| 7,137,389 B2 | 11/2006 | Berthon-Jones |
| 7,152,598 B2 | 12/2006 | Morris et al. |
| 7,168,429 B2 | 1/2007 | Matthews et al. |
| 7,195,028 B2 | 3/2007 | Basset et al. |
| 7,210,478 B2 | 5/2007 | Banner et |
| 7,229,430 B2 | 6/2007 | Hickle et al. |
| 7,267,122 B2 | 9/2007 | Hill |
| 7,270,126 B2 | 9/2007 | Wallace et al. |
| 7,275,540 B2 | 10/2007 | Bolam et al. |
| 7,296,573 B2 | 11/2007 | Estes et al. |
| 7,297,119 B2 | 11/2007 | Westbrook et al. |
| 7,331,343 B2 | 2/2008 | Schmidt et al. |
| 7,353,824 B1 | 4/2008 | Forsyth et al. |
| 7,367,337 B2 | 5/2008 | Berthon-Jones et al. |
| 7,369,757 B2 | 5/2008 | Farbarik |
| 7,370,650 B2 | 5/2008 | Nadjafizadeh et al. |
| 7,398,115 B2 | 7/2008 | Lynn |
| 7,406,870 B2 | 8/2008 | Seto |
| 7,428,902 B2 | 9/2008 | Du et al. |
| 7,448,381 B2 | 11/2008 | Sasaki et al. |
| 7,455,583 B2 | 11/2008 | Taya |
| 7,460,959 B2 | 12/2008 | Jafari |
| 7,475,685 B2 | 1/2009 | Dietz et al. |
| 7,487,773 B2 | 2/2009 | Li |
| 7,509,957 B2 | 3/2009 | Duquette et al. |
| 7,527,056 B2 | 5/2009 | Turiello |
| 7,533,671 B2 | 5/2009 | Gonzalez et al. |
| 7,621,269 B2 | 11/2009 | Turiello |
| 7,644,713 B2 | 1/2010 | Berthon-Jones |
| 7,654,802 B2 | 2/2010 | Crawford, Jr. et al. |
| 7,661,428 B2 | 2/2010 | Berthon-Jones |
| 7,673,629 B2 | 3/2010 | Turiello |
| 7,677,247 B2 | 3/2010 | Turiello |
| 7,694,677 B2 | 4/2010 | Tang |
| 7,694,678 B2 | 4/2010 | Turiello |
| 7,717,112 B2 | 5/2010 | Sun et al. |
| 7,717,113 B2 | 5/2010 | Andrieux |
| D618,356 S | 6/2010 | Ross |
| 7,770,578 B2 | 8/2010 | Estes et al. |
| 7,784,461 B2 | 8/2010 | Figueiredo et al. |
| 7,810,496 B2 | 10/2010 | Estes et al. |
| 7,810,497 B2 | 10/2010 | Pittman et al. |
| 7,814,906 B2 | 10/2010 | Moretti |
| 7,823,588 B2 | 11/2010 | Hansen |
| 7,827,988 B2 | 11/2010 | Matthews et al. |
| 7,855,716 B2 | 12/2010 | McCreary et al. |
| 7,856,979 B2 | 12/2010 | Doshi et al. |
| D632,796 S | 2/2011 | Ross et al. |
| D632,797 S | 2/2011 | Ross et al. |
| 7,882,835 B2 | 2/2011 | Eger et al. |
| 7,886,739 B2 | 2/2011 | Soliman et al. |
| 7,886,740 B2 | 2/2011 | Thomas et al. |
| 7,891,354 B2 | 2/2011 | Farbarik |
| 7,893,560 B2 | 2/2011 | Carter |
| 7,905,231 B2 | 3/2011 | Chalvignac |
| 7,918,222 B2 | 4/2011 | Chen |
| 7,918,223 B2 | 4/2011 | Soliman et al. |
| 7,920,067 B2 | 4/2011 | Durtschi et al. |
| 7,928,852 B2 | 4/2011 | Durtschi et al. |
| D638,852 S | 5/2011 | Skidmore et al. |
| 7,934,499 B2 | 5/2011 | Berthon-Jones |

(56) References Cited

U.S. PATENT DOCUMENTS

| | | |
|---|---|---|
| 7,938,114 B2 | 5/2011 | Matthews et al. |
| 7,963,283 B2 | 6/2011 | Sinderby |
| 7,984,712 B2 | 7/2011 | Soliman et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| 8,002,154 B2 | 8/2011 | Fontela et al. |
| D645,158 S | 9/2011 | Sanchez et al. |
| 8,021,309 B2 | 9/2011 | Zilberg |
| 8,021,310 B2 | 9/2011 | Sanborn et al. |
| 8,033,280 B2 | 10/2011 | Heinonen |
| D649,157 S | 11/2011 | Skidmore et al. |
| 8,051,853 B2 | 11/2011 | Berthon-Jones |
| 8,070,709 B2 | 12/2011 | Childers |
| 8,083,677 B2 | 12/2011 | Rohde |
| D652,521 S | 1/2012 | Ross et al. |
| D652,936 S | 1/2012 | Ross et al. |
| 8,105,310 B2 | 1/2012 | Klein |
| D653,749 S | 2/2012 | Winter et al. |
| 8,113,062 B2 | 2/2012 | Graboi et al. |
| 8,122,885 B2 | 2/2012 | Berthon-Jones et al. |
| D655,405 S | 3/2012 | Winter et al. |
| D655,809 S | 3/2012 | Winter et al. |
| D656,237 S | 3/2012 | Sanchez et al. |
| 8,136,521 B2 | 3/2012 | Matthews et al. |
| 8,152,116 B2 | 4/2012 | Westberg |
| RE43,398 E | 5/2012 | Honkonen et al. |
| 8,181,643 B2 | 5/2012 | Friedberg |
| 8,181,648 B2 | 5/2012 | Perine et al. |
| 8,181,649 B2 | 5/2012 | Brunner |
| 8,187,184 B2 | 5/2012 | Muller et al. |
| 8,210,173 B2 | 7/2012 | Vandine |
| 8,210,174 B2 | 7/2012 | Farbarik |
| 8,211,128 B1 | 7/2012 | Facundus et al. |
| 8,216,159 B1 | 7/2012 | Leiboff |
| 8,217,218 B2 | 7/2012 | Court et al. |
| 8,225,796 B2 | 7/2012 | Davenport et al. |
| 8,235,930 B1 | 8/2012 | McCall |
| 8,240,684 B2 | 8/2012 | Ross et al. |
| 8,251,923 B2 | 8/2012 | Carrez et al. |
| 8,256,418 B2 | 9/2012 | Bassin |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,288,607 B2 | 10/2012 | Court et al. |
| 8,302,600 B2 | 11/2012 | Andrieux et al. |
| 8,302,602 B2 | 11/2012 | Andrieux et al. |
| 2002/0014240 A1 | 2/2002 | Truschel |
| 2002/0053345 A1 | 5/2002 | Jafari et al. |
| 2002/0185126 A1 | 12/2002 | Krebs |
| 2003/0010339 A1 | 1/2003 | Banner et al. |
| 2003/0158466 A1 | 8/2003 | Lynn et al. |
| 2003/0159695 A1 | 8/2003 | Younes |
| 2003/0221689 A1 | 12/2003 | Berthon-Jones |
| 2004/0050387 A1 | 3/2004 | Younes |
| 2004/0074492 A1 | 4/2004 | Berthon-Jones |
| 2004/0089561 A1 | 5/2004 | Herman |
| 2004/0163648 A1 | 8/2004 | Burton |
| 2004/0187870 A1 | 9/2004 | Matthews et al. |
| 2005/0039748 A1 | 2/2005 | Andrieux |
| 2005/0109340 A1 | 5/2005 | Tehrani |
| 2005/0139212 A1 | 6/2005 | Bourdon |
| 2005/0172965 A1 | 8/2005 | Thulin |
| 2005/0188991 A1 | 9/2005 | Sun et al. |
| 2005/0241639 A1 | 11/2005 | Zilberg |
| 2006/0000475 A1 | 1/2006 | Matthews et al. |
| 2006/0011200 A1 | 1/2006 | Remmers et al. |
| 2006/0086357 A1 | 4/2006 | Soliman et al. |
| 2006/0102180 A1 | 5/2006 | Berthon-Jones |
| 2006/0112959 A1 | 6/2006 | Mechlenburg et al. |
| 2006/0118112 A1 | 6/2006 | Cattano et al. |
| 2006/0144144 A1 | 7/2006 | Seto |
| 2006/0150974 A1 | 7/2006 | Berthon-Jones |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0174883 A1 | 8/2006 | Aylsworth et al. |
| 2006/0189880 A1 | 8/2006 | Lynn et al. |
| 2006/0195041 A1 | 8/2006 | Lynn et al. |
| 2006/0201505 A1 | 9/2006 | Remmers et al. |
| 2006/0217633 A1 | 9/2006 | Glocker et al. |
| 2006/0235324 A1 | 10/2006 | Lynn |
| 2006/0241708 A1 | 10/2006 | Boute |
| 2006/0247508 A1 | 11/2006 | Fennell |
| 2006/0249150 A1 | 11/2006 | Dietz et al. |
| 2006/0249156 A1 | 11/2006 | Moretti |
| 2006/0254588 A1 | 11/2006 | Brewer et al. |
| 2006/0264762 A1 | 11/2006 | Starr |
| 2006/0272642 A1 | 12/2006 | Chalvignac |
| 2006/0278218 A1 | 12/2006 | Hoffman |
| 2007/0000494 A1 | 1/2007 | Banner et al. |
| 2007/0017515 A1 | 1/2007 | Wallace et al. |
| 2007/0027375 A1 | 2/2007 | Melker et al. |
| 2007/0028921 A1 | 2/2007 | Banner et al. |
| 2007/0044796 A1 | 3/2007 | Zdrojkowski et al. |
| 2007/0068530 A1 | 3/2007 | Pacey |
| 2007/0072541 A1 | 3/2007 | Daniels, II et al. |
| 2007/0077200 A1 | 4/2007 | Baker |
| 2007/0089738 A1 | 4/2007 | Soliman et al. |
| 2007/0093721 A1 | 4/2007 | Lynn et al. |
| 2007/0101992 A1 | 5/2007 | Soliman et al. |
| 2007/0129647 A1 | 6/2007 | Lynn |
| 2007/0135736 A1 | 6/2007 | Addington et al. |
| 2007/0144522 A1 | 6/2007 | Eger et al. |
| 2007/0149860 A1 | 6/2007 | Lynn et al. |
| 2007/0157931 A1 | 7/2007 | Parker et al. |
| 2007/0163579 A1 | 7/2007 | Li et al. |
| 2007/0191688 A1 | 8/2007 | Lynn |
| 2007/0191697 A1 | 8/2007 | Lynn et al. |
| 2007/0215154 A1 | 9/2007 | Borrello |
| 2007/0221224 A1 | 9/2007 | Pittman et al. |
| 2007/0227537 A1 | 10/2007 | Bemister et al. |
| 2007/0251532 A1 | 11/2007 | Friedberg |
| 2007/0272241 A1 | 11/2007 | Sanborn et al. |
| 2007/0277823 A1 | 12/2007 | Al-Ali et al. |
| 2007/0283958 A1 | 12/2007 | Naghavi |
| 2007/0284361 A1 | 12/2007 | Nadjafizadeh et al. |
| 2008/0000478 A1 | 1/2008 | Matthiessen et al. |
| 2008/0000479 A1 | 1/2008 | Elaz et al. |
| 2008/0041382 A1 | 2/2008 | Matthews et al. |
| 2008/0041383 A1 | 2/2008 | Matthews et al. |
| 2008/0051674 A1 | 2/2008 | Davenport et al. |
| 2008/0053441 A1 | 3/2008 | Gottlib et al. |
| 2008/0053442 A1 | 3/2008 | Estes et al. |
| 2008/0053443 A1 | 3/2008 | Estes et al. |
| 2008/0053444 A1 | 3/2008 | Estes et al. |
| 2008/0066752 A1 | 3/2008 | Baker et al. |
| 2008/0066753 A1 | 3/2008 | Martin et al. |
| 2008/0072896 A1 | 3/2008 | Setzer et al. |
| 2008/0072902 A1 | 3/2008 | Setzer et al. |
| 2008/0078390 A1 | 4/2008 | Milne et al. |
| 2008/0081974 A1 | 4/2008 | Pav |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2008/0168988 A1 | 7/2008 | Lu |
| 2008/0178880 A1 | 7/2008 | Christopher et al. |
| 2008/0178882 A1 | 7/2008 | Christopher et al. |
| 2008/0185002 A1 | 8/2008 | Berthon-Jones et al. |
| 2008/0200775 A1 | 8/2008 | Lynn |
| 2008/0200819 A1 | 8/2008 | Lynn et al. |
| 2008/0221469 A1 | 9/2008 | Shevchuk |
| 2008/0251079 A1 | 10/2008 | Richey |
| 2008/0295837 A1 | 12/2008 | McCormick et al. |
| 2008/0302359 A1 | 12/2008 | Loomas et al. |
| 2009/0014007 A1 | 1/2009 | Brambilla et al. |
| 2009/0050153 A1 | 2/2009 | Brunner |
| 2009/0082653 A1 | 3/2009 | Rohde |
| 2009/0088613 A1 | 4/2009 | Marttila et al. |
| 2009/0093697 A1 | 4/2009 | Mir et al. |
| 2009/0137927 A1 | 5/2009 | Miller |
| 2009/0149730 A1 | 6/2009 | McCrary |
| 2009/0165795 A1 | 7/2009 | Nadjafizadeh et al. |

(56) References Cited

U.S. PATENT DOCUMENTS

| | | |
|---|---|---|
| 2009/0171176 A1 | 7/2009 | Andersohn |
| 2009/0171226 A1 | 7/2009 | Campbell et al. |
| 2009/0178675 A1 | 7/2009 | Turiello |
| 2009/0178676 A1 | 7/2009 | Villax et al. |
| 2009/0194100 A1 | 8/2009 | Minagi |
| 2009/0205661 A1 | 8/2009 | Stephenson et al. |
| 2009/0205663 A1 | 8/2009 | Vandine et al. |
| 2009/0229605 A1 | 9/2009 | Efrati et al. |
| 2009/0241951 A1 | 10/2009 | Jafari et al. |
| 2009/0241952 A1 | 10/2009 | Nicolazzi et al. |
| 2009/0241953 A1 | 10/2009 | Vandine et al. |
| 2009/0241955 A1 | 10/2009 | Jafari et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247891 A1 | 10/2009 | Wood |
| 2009/0250061 A1 | 10/2009 | Marasigan |
| 2009/0272382 A1 | 11/2009 | Euliano et al. |
| 2009/0281481 A1 | 11/2009 | Harding |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2009/0308398 A1 | 12/2009 | Ferdinand et al. |
| 2009/0314294 A1 | 12/2009 | Chalvignac |
| 2009/0318851 A1 | 12/2009 | Schenck |
| 2010/0011307 A1 | 1/2010 | Desfossez et al. |
| 2010/0018529 A1 | 1/2010 | Chalvignac |
| 2010/0024819 A1 | 2/2010 | Tiedje |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0065057 A1 | 3/2010 | Berthon-Jones |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078018 A1 | 4/2010 | Heinonen |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0081958 A1 | 4/2010 | She |
| 2010/0101574 A1 | 4/2010 | Bassin |
| 2010/0101576 A1 | 4/2010 | Berthon-Jones |
| 2010/0116276 A1 | 5/2010 | Bayasi |
| 2010/0137737 A1 | 6/2010 | Addington et al. |
| 2010/0139660 A1 | 6/2010 | Adahan |
| 2010/0186741 A1 | 7/2010 | Aylsworth et al. |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0234758 A1 | 9/2010 | de Menezes |
| 2010/0236553 A1 | 9/2010 | Jafari et al. |
| 2010/0236555 A1 | 9/2010 | Jafari et al. |
| 2010/0242961 A1 | 9/2010 | Mougel et al. |
| 2010/0252048 A1 | 10/2010 | Young et al. |
| 2010/0258123 A1 | 10/2010 | Somaiya et al. |
| 2010/0262038 A1 | 10/2010 | Tan et al. |
| 2010/0282259 A1 | 11/2010 | Figueiredo et al. |
| 2010/0288283 A1 | 11/2010 | Campbell et al. |
| 2010/0300446 A1 | 12/2010 | Nicolazzi et al. |
| 2010/0331768 A1 | 12/2010 | Hedmann et al. |
| 2011/0011400 A1 | 1/2011 | Gentner et al. |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0034863 A1 | 2/2011 | Hoffa |
| 2011/0041849 A1 | 2/2011 | Chen et al. |
| 2011/0041850 A1 | 2/2011 | Vandine et al. |
| 2011/0061648 A1 | 3/2011 | Durtschi et al. |
| 2011/0071367 A1 | 3/2011 | Court et al. |
| 2011/0077549 A1 | 3/2011 | Kitai et al. |
| 2011/0100373 A1 | 5/2011 | Efrati et al. |
| 2011/0125052 A1 | 5/2011 | Davenport et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132363 A1 | 6/2011 | Chalvignac |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0178427 A1 | 7/2011 | Tan et al. |
| 2011/0196251 A1 | 8/2011 | Jourdain et al. |
| 2011/0201956 A1 | 8/2011 | Alferness et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0220112 A1 | 9/2011 | Connor |
| 2011/0226250 A1 | 9/2011 | LaBollita et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2011/0284003 A1 | 11/2011 | Douglas et al. |
| 2011/0290246 A1 | 12/2011 | Zachar |
| 2011/0293706 A1 | 12/2011 | Ludwig et al. |
| 2011/0313689 A1 | 12/2011 | Holley et al. |
| 2012/0000466 A1 | 1/2012 | Rapoport |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0006328 A1 | 1/2012 | Berthon-Jones |
| 2012/0022441 A1 | 1/2012 | Kelly et al. |
| 2012/0029317 A1 | 2/2012 | Doyle et al. |
| 2012/0030611 A1 | 2/2012 | Skidmore |
| 2012/0060835 A1 | 3/2012 | Mashak |
| 2012/0060841 A1 | 3/2012 | Crawford, Jr. et al. |
| 2012/0065533 A1 | 3/2012 | Carrillo, Jr. et al. |
| 2012/0071729 A1 | 3/2012 | Doyle et al. |
| 2012/0083729 A1 | 4/2012 | Childers |
| 2012/0090610 A1 | 4/2012 | O'Connor et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0139734 A1 | 6/2012 | Olde et al. |
| 2012/0150057 A1 | 6/2012 | Mantri |
| 2012/0167885 A1 | 7/2012 | Masic et al. |
| 2012/0185792 A1 | 7/2012 | Kimm et al. |

(56) References Cited

U.S. PATENT DOCUMENTS

| | | |
|---|---|---|
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0215081 A1 | 8/2012 | Euliano et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0304997 A1 | 12/2012 | Jafari et al. |
| 2013/0186400 A1 | 7/2013 | Jafari et al. |
| 2013/0186401 A1 | 7/2013 | Jafari et al. |

FOREIGN PATENT DOCUMENTS

| | | |
|---|---|---|
| EP | 1270036 | 1/2003 |
| WO | WO 94/23780 A | 10/1994 |
| WO | WO 98/06449 A | 2/1998 |
| WO | WO 00/10634 A | 3/2000 |
| WO | WO 00/45880 A | 8/2000 |
| WO | WO 01/74430 A | 10/2001 |
| WO | WO 02/28460 A | 4/2002 |
| WO | WO 03/055552 A1 | 7/2003 |
| WO | WO 2004000114 | 12/2003 |
| WO | WO 2004/084980 A | 10/2004 |
| WO | WO 2005/105189 | 11/2005 |
| WO | WO 2006/137784 A1 | 12/2006 |
| WO | WO 2007145948 | 12/2007 |
| WO | WO 2009123981 | 10/2009 |

OTHER PUBLICATIONS

PCT International Search Report and Written Opinion in Application PCT/US09/038811, mailed Jun. 7, 2009, 13 pgs.
PCT International Search Report and Written Opinion in Application PCT/US2009038818, mailed Jul. 14, 2009, 15 pgs.
PCT International Search Report and Written Opinion in Application PCT/2009/038815, mailed Jul. 1, 2009, 14 pgs.
PCT International Search Report and Written Opinion in Application PCT/2009/038810, mailed Jul. 6, 2009, 16 pgs.
PCT International Search Report and Written Opinion in Application PCT/US2009/038820, mailed Jul. 22, 2009, 14 pgs.
PCT International Search Report and Written Opinion in Application PCT/US2009/038819, mailed Jun. 26, 2009, 12 pgs.
U.S. Appl. No. 12/242,756, Supplemental Notice of Allowability mailed Aug. 27, 2012, 2 pgs.
U.S. Appl. No. 12/242,741, Supplemental Notice of Allowability mailed Aug. 27, 2012, 2 pgs.
U.S. Appl. No. 12/408,414, Amendment and Response filed Sep. 5, 2012, 7 pgs.
U.S. Appl. No. 12/414,419, Amendment and Response filed Aug. 27, 2012, 8 pgs.
U.S. Appl. No. 12/242,741, Notice of Allowance mailed Jun. 5, 2012, 5 pgs.
U.S. Appl. No. 12/242,756, Notice of Allowance mailed Jun. 5, 2012, 5 pgs.
U.S. Appl. No. 12/408,408, Notice of Allowance mailed Jun. 4, 2012, 10 pgs.
U.S. Appl. No. 12/408,414, Office Action mailed Jun. 20, 2012, 9 pgs.
U.S. Appl. No. 12/414,419, Office Action mailed Jul. 18, 2012, 16 pgs.
PCT International Search Report and Written Opinion in Application PCT/US2010/025485, mailed Feb. 27, 2009, 8 pgs.
U.S. Appl. No. 12/242,741, Office Action mailed Jan. 10, 2012, 7 pgs.
U.S. Appl. No. 12/242,756, Office Action mailed Jan. 10, 2012, 7 pgs.
U.S. Appl. No. 12/414,419, Office Action mailed Jan. 20, 2012, 15 pgs.
Younes, M, et al., "Control of breathing relevant to mechanical ventilation", in Physiological Basis of Ventilatory Support, J.J. Marini and A.S. Slutsky, Ed., New York, Marcel Dekker, 1998, pp. 1-73.
Crooke, P.S. et al., "Patient-ventilator interaction: A general model for nonpassive mechanical ventilation", 1998, AMA Journal of Mathematics Applied in Medicine and Biology, 15, pp. 321-337.
U.S. Appl. No. 12/238,248, Office Action mailed Apr. 26, 2013, 13 pgs.
U.S. Appl. No. 12/395,332, Notice of Allowance mailed Dec. 24, 2012, 8 pgs.
U.S. Appl. No. 12/408,414, Notice of Allowance mailed Dec. 10, 2012, 10 pgs.
U.S. Appl. No. 12/414,419, Notice of Allowance mailed Jan. 8, 2013, 7 pgs.
U.S. Appl. No. 12/238,248, Advisory Action mailed Jan. 4, 2013, 3 pgs.
U.S. Appl. No. 13/565,595, Notice of Allowance mailed Feb. 25, 2013, 8 pgs.
Jafari, M. et al., "Robust Feedback Design for Proportional Assist Ventilation-System Dynamics and Problem Definition" Decision and Control, 2005 and 2005 European Control Conference. CDC-E CC '05. 44th IEEE Conference on Seville, Spain Dec. 12-15, 2005 (Dec. 12, 2005), pp. 4839-4844, XP010884460 DISBN: 978-0-7803-9567-1, the whole document.
U.S. Appl. No. 12/238,248, Office Action mailed Oct. 15, 2012, 12 pgs.
U.S. Appl. No. 12/238,248, Office Action mailed May 14, 2012, 12 pgs.
U.S. Appl. No. 12/395,332, Office Action mailed Sep. 13, 2012, 9 pgs.
U.S. Appl. No. 12/414,419, Notice of Allowance mailed Sep. 19, 2012, 8 pgs.
U.S. Appl. No. 13/565,595, Notice of Allowance mailed Nov. 2, 2012, 12 pgs.

* cited by examiner

DETERMINATION OF PATIENT CIRCUIT DISCONNECT IN LEAK-COMPENSATED VENTILATORY SUPPORT

BACKGROUND

Medical ventilators may determine when a patient is connected to the system in order to deliver specified therapy and synchronize the operation of the ventilator with the natural breathing of the patient. During ventilation, certain levels of leak rate may be unavoidable or allowed and this should not prematurely result in a patient disconnect determination. Furthermore, it is now common for medical ventilators to compensate for leaks in the ventilation system in order to accurately synchronize the therapy with the patient's breathing cycle as well as provide therapy that compensates for the leaks.

Detection and declaration of the disconnection of a patient from the ventilation system during therapy is a feature provided by some ventilators. Some ventilators are provided with a disconnect alarm that notifies caregivers when a patient is no longer connected to the ventilation system. Depending on how a ventilator compensates for leaks, this can impair the ability of the ventilator to accurate detect patient disconnect and provide an alarm to caregivers while allowing unimpeded therapy under acceptable leak conditions.

SUMMARY

This disclosure describes systems and methods for compensating for pressure-dependent elastic sources of leaks in a ventilation system. The disclosure describes a novel model and algorithm to incorporate the operator's maximum system leak allowed and avoids nuisance alarms caused by occasional and/or transient variations in leak rate caused by changing circuit pressure and/or patient behavior.

In part, this disclosure describes a method of detecting disconnection of a ventilation system during delivery of gas from a medical ventilator to a patient. The method includes developing an actual leakage equation describing leakage from the ventilation system as a function of pressure in the ventilation system and developing a maximum leakage equation describing a maximum allowed leakage from the ventilation system as a function of pressure in the ventilation system. At least one pressure in the ventilation system is monitored during delivery of gas to the patient during a breath. The method further includes calculating an actual leakage from the ventilation system during the breath based on the current pressure using the actual leakage equation and calculating a maximum allowed leakage from the ventilation system during the breath based on the current pressure using the maximum leakage equation. The method then compares the calculated maximum allowed leakage and the actual leakage and makes a determination of whether the ventilator has become disconnected from the patient based on the results of the comparison.

The disclosure also describes another method of detecting disconnection of a ventilation system during delivery of therapy to a patient. The method includes generating an actual leak equation based on a leak model and measurements taken during the delivery of therapy to the patient and generating a maximum leak equation based on the leak model, and a maximum allowed leakage at a specified pressure. The method measures pressure in the ventilation system during a current therapy period. The method further calculates an actual leak from the ventilation system for the current therapy period based on the pressure using the actual leak equation and calculates a maximum allowable leak from the ventilation system for the current therapy period based on the pressure using the maximum leak equation. The method then selects, based on a comparison of the calculated actual leak and the maximum allowable leak, one of at least two ventilator connection states, such as the ventilator is connected or is disconnected.

Yet another aspect of this disclosure describes a pressure support system that includes: a pressure generating system adapted to generate a flow of breathing gas; a ventilation system including a patient interface device; one or more sensors operatively coupled to the pressure generating system or the ventilation system, each sensor capable of generating an output indicative of a pressure of the breathing gas; a processor; an actual leak estimation module that calculates actual leakage in the ventilation system based on pressure and a predetermined actual leak equation; a maximum allowable leak estimation module that calculates maximum allowable leakage in the ventilation system based on pressure and a predetermined maximum allowable leak equation; and a disconnect monitoring module that generates one or more alarms based on a comparison of the actual leakage and the maximum allowable leakage.

The disclosure further describes a controller for a medical ventilator that includes a microprocessor and a disconnect monitoring module. The disconnect monitoring module determines if the medical ventilator is disconnected from a patient based on an actual leakage estimate and a maximum allowable leakage estimate, in which the actual leakage estimate is calculated using a first equation based on pressure in a ventilation system and the maximum allowable leakage estimate is calculated using a second equation different from the first equation based on the pressure in the ventilation system.

In yet another aspect, the disclosure describes a computer-readable medium storing computer-executable instruction for performing a method of detecting disconnection of a ventilation system during delivery of therapy to a patient. The method includes generating an actual leak equation based on a leak model and measurements taken during the delivery of therapy to the patient and generating a maximum leak equation based on the leak model, and a maximum allowed leakage at a specified pressure. The method measures pressure in the ventilation system during a current therapy period. Based on the measurements, the method then calculates an actual leak from the ventilation system for the current therapy period based on the pressure using the actual leak equation and calculates a maximum allowable leak from the ventilation system for the current therapy period based on the pressure using the maximum leak equation. The method then selects, based on a comparison of the actual leak and the maximum allowable leak, one of at least two ventilator connection states.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which form a part of this application, are illustrative of described technology and are not meant to limit the scope of the invention as claimed in any manner, which scope shall be based on the claims appended hereto.

DETAILED DESCRIPTION

Although the techniques introduced above and discussed in detail below may be implemented for a variety of medical devices, the present disclosure will discuss the implementation of these techniques in the context of a medical ventilator for use in providing ventilation support to a human patient. The reader will understand that the technology described in the context of a medical ventilator for human patients could be adapted for use with other systems such as ventilators for non-human patients and general gas transport systems in which compensating for leaks may interfere with determining that the system is disconnected.

Figure 1:
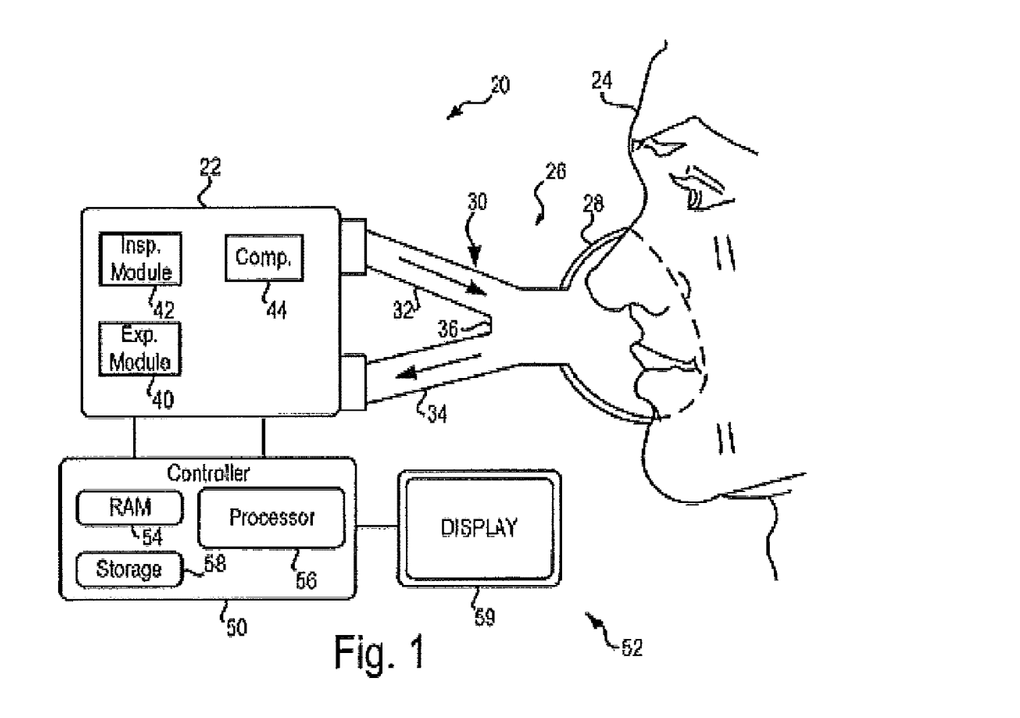
FIG. 1 illustrates an embodiment of a ventilator connected to a human patient.

FIG. 1 illustrates an embodiment of a ventilator 20 connected to a human patient 24. Ventilator 20 includes a pneumatic system 22 (also referred to as a pressure generating system 22) for circulating breathing gases to and from patient 24 via the ventilation tubing system 26, which couples the patient to the pneumatic system via physical patient interface 28 and ventilator circuit 30. Ventilator circuit 30 could be a two-limb or one-limb circuit for carrying gas to and from the patient. In a two-limb embodiment as shown, a wye fitting 36 may be provided as shown to couple the patient interface 28 to the inspiratory limb 32 and the expiratory limb 34 of the circuit 30.

The present systems and methods have proved particularly advantageous in noninvasive settings, such as with facial breathing masks, as those settings typically are more susceptible to leaks. However, leaks do occur in a variety of settings, and the present description contemplates that the patient interface may be invasive or non-invasive, and of any configuration suitable for communicating a flow of breathing gas from the patient circuit to an airway of the patient. Examples of suitable patient interface devices include a nasal mask, nasal/oral mask (which is shown in FIG. 1), nasal prong, full-face mask, tracheal tube, endotracheal tube, nasal pillow, etc. Pneumatic system 22 may be configured in a variety of ways. In the present example, system 22 includes an expiratory module 40 coupled with an expiratory limb 34 and an inspiratory module 42 coupled with an inspiratory limb 32. Compressor 44 or another source or sources of pressurized gas (e.g., air and oxygen) is coupled with inspiratory module 42 to provide a source of pressurized breathing gas for ventilatory support via inspiratory limb 32.

The pneumatic system may include a variety of other components, including sources for pressurized air and/or oxygen, mixing modules, valves, sensors, tubing, accumulators, filters, etc. Controller 50 is operatively coupled with pneumatic system 22, signal measurement and acquisition systems, and an operator interface 52 may be provided to enable an operator to interact with the ventilator (e.g., change ventilator settings, select operational modes, view monitored parameters, etc.). Controller 50 may include memory 54, one or more processors 56, storage 58, and/or other components of the type commonly found in command and control computing devices.

The memory 54 is computer-readable storage media that stores software that is executed by the processor 56 and which controls the operation of the ventilator 20. In an embodiment, the memory 54 comprises one or more solid-state storage devices such as flash memory chips. In an alternative embodiment, the memory 54 may be mass storage connected to the processor 56 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 56. Computer-readable storage media includes volatile and non-volatile, removable and non-removable media implemented in any method or technology for storage of information such as computer-readable instructions, data structures, program modules or other data. Computer-readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

As described in more detail below, controller 50 issues commands to pneumatic system 22 in order to control the breathing assistance provided to the patient by the ventilator. The specific commands may be based on inputs received from patient 24, pneumatic system 22 and sensors, operator interface 52 and/or other components of the ventilator. In the depicted example, operator interface includes a display 59 that is touch-sensitive, enabling the display to serve both as an input and output device.

Figure 2:
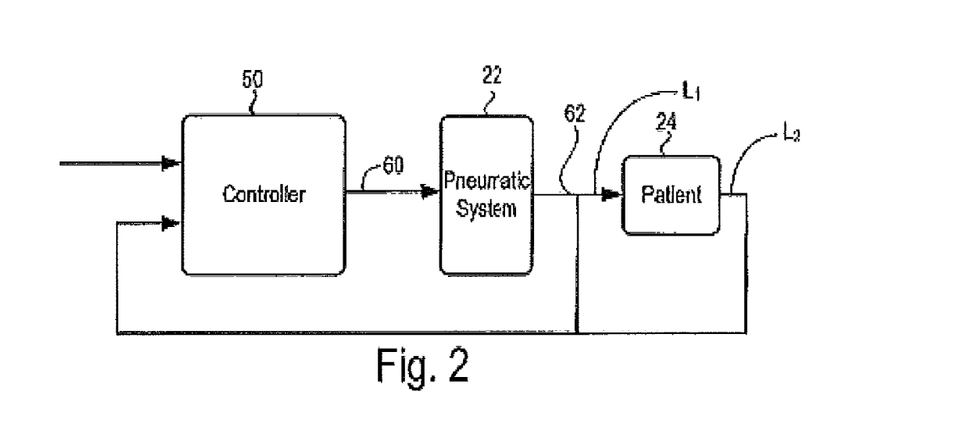
FIG. 2 schematically depicts exemplary systems and methods of ventilator control.

FIG. 2 schematically depicts exemplary systems and methods of ventilator control. As shown, controller 50 issues control commands 60 to drive pneumatic system 22 and thereby circulate breathing gas to and from patient 24. The depicted schematic interaction between pneumatic system 22 and patient 24 may be viewed in terms of pressure and/or flow "signals." For example, signal 62 may be an increased pressure which is applied to the patient via inspiratory limb 32. Control commands 60 are based upon inputs received at controller 50 which may include, among other things, inputs from operator interface 52, and feedback from pneumatic system 22 (e.g., from pressure/flow sensors) and/or sensed from patient 24.

In many cases, it may be desirable to establish a baseline pressure and/or flow trajectory for a given respiratory therapy (e.g., a particular cycle or session). The volume of breathing gas delivered to the patients lung ($L_1$) and the volume of the gas exhaled by the patient ($L_2$) are measured or determined, and the measured or predicted/estimated leaks are accounted for to ensure accurate delivery and data reporting and monitoring. Accordingly, the more accurate the leak estimation, the better the baseline calculation of delivered and exhaled volume as well as event detection (triggering and cycling phase transitions).

When modeling the delivery of gas to and from a patient 24 via a closed-circuit ventilator, one simple assumption is that compliance of the ventilator circuit 30 is fixed and that all gas injected into the ventilator circuit 30 that does not exit the circuit 30 via the expiratory limb 34 fills the circuit as well as the patient's lungs and causes an increase in pressure. As gas is injected ($L_1$), the lung responds to the increased gas pressure in the circuit 30 by expanding. The amount the lung expands is proportional to the lung compliance and is modeled as a function of gas pressure differential (Compliance=volume delivered/pressure difference).

The term circuit compliance is used to refer to the amount the pressure in the ventilator circuit 30 (or ventilator circuit 30 and attached patient interface 28, depending on how the compliance is determined) changes based on changes in volume delivered into the circuit. In an embodiment, the circuit compliance may be estimated by pressurizing the ventilator circuit 30 (or circuit 30 and interface 28 combination) when flow to the patient is blocked and measuring the volume of additional gas introduced to cause the pressure change (compliance=volume delivered/pressure difference).

The term circuit resistance is used to refer to the amount the pressure changes between two sites upstream and downstream the ventilator circuit as a function of volumetric flow rate through that circuit. Tubing resistance may be modeled as a two-parameter function of flow:

$$\text{Pressure difference } K_1 * \text{Flow} + K_2 * \text{Flow}^2 = \text{Flow} * (K_1 + K_2 * \text{Flow})$$

In which $K_1$ and $K_2$ are empirically derived constants. For example, in an embodiment, the circuit resistance may be estimated by passing several fixed flow rates through the circuit and measuring the pressure difference between certain upstream and downstream sites and finding the best curve fit to the collected data.

Such methods of determining compliance and resistance may be executed by the operator prior to attaching the patient to the ventilator as part of the set up of the ventilator 20 to provide therapy. Other methods of determining compliance and/or resistance are also possible and could be adapted for use with the disclosed leak-compensation systems and methods described herein.

Errors may be introduced due to leaks in the ventilation tubing system 26. The term ventilation tubing system 26 is used herein to describe the ventilator circuit 30, any equipment attached to or used in the ventilator circuit 30 such as water traps, monitors, drug delivery devices, etc. (not shown), and the patient interface 28. Depending on the embodiment, this may include some equipment contained in the inspiration module 42 and/or the expiration module 40. When referring to leaks in or from the ventilation tubing system 26, such leaks include leaks within the system 26 and leaks where the system 26 connects to the pressure generator 22 or the patient 24. Thus, leaks from the ventilation tubing system 26 include leaks from the ventilator circuit 30, leaks from the patient interface 28 (e.g., masks are often provided with holes or other pressure relief devices through which some leakage may occur), leaks from the point of connection of the patient interface 28 to the patient 24 (e.g., leaks around the edges of a mask due to a poor fit or patient movement), and leaks from the point of connection of the patient interface 28 to the circuit 30 (e.g., due to a poor connection between the patient interface 28 and the circuit 30).

For the purpose of estimating how a leak flow rate changes based on changes in pressure in the ventilation tubing system 26, the instantaneous leak may be modeled as a leak through a single inelastic orifice or opening of a fixed size in which that size is determined based on comparing the total volume into the inspiratory limb 32 and out of the expiratory limb 34. However, this leak model does not take into account any elastic component of leak source(s) in the system 26, that is how much the area of any of the holes or openings in the ventilation system 26 through which leakage occurs may change due to an increase or decrease in pressure.

It has been determined that not accounting for elastic leakage from the ventilation tubing system 26 can cause many problems. First, if only the inelastic/fixed orifice model is used to estimate leak, the subsequent errors caused by ignoring the elastic effects of any actual leaks end up generating inaccurate estimates of flow rates into the lung. This can cause the ventilator 20 to estimate gas volume delivered into the lung inaccurately when, in fact, the elastic leaks in the system 26 have let more gas escape than estimated. Second, if the elasticity of the leak source is ignored, any other calculation, estimate, or action that the ventilator 20 may perform which is affected by the leak estimate will be less accurate.

In the systems and methods described herein, the identification of the disconnection of the ventilation system from the patient during ventilation therapy is made more accurate by compensating the disconnect condition to account for the both the fixed (rigid) and elastic components of the system leakage. This results in a more accurate and timely triggering of the disconnect condition by the ventilator 20. While the systems and methods are presented in the context of identifying a disconnect condition during ventilator therapy, the technology described herein could be used to identify disconnect conditions in any gas flow system in which some leakage is expected and tolerated.

Figure 3:
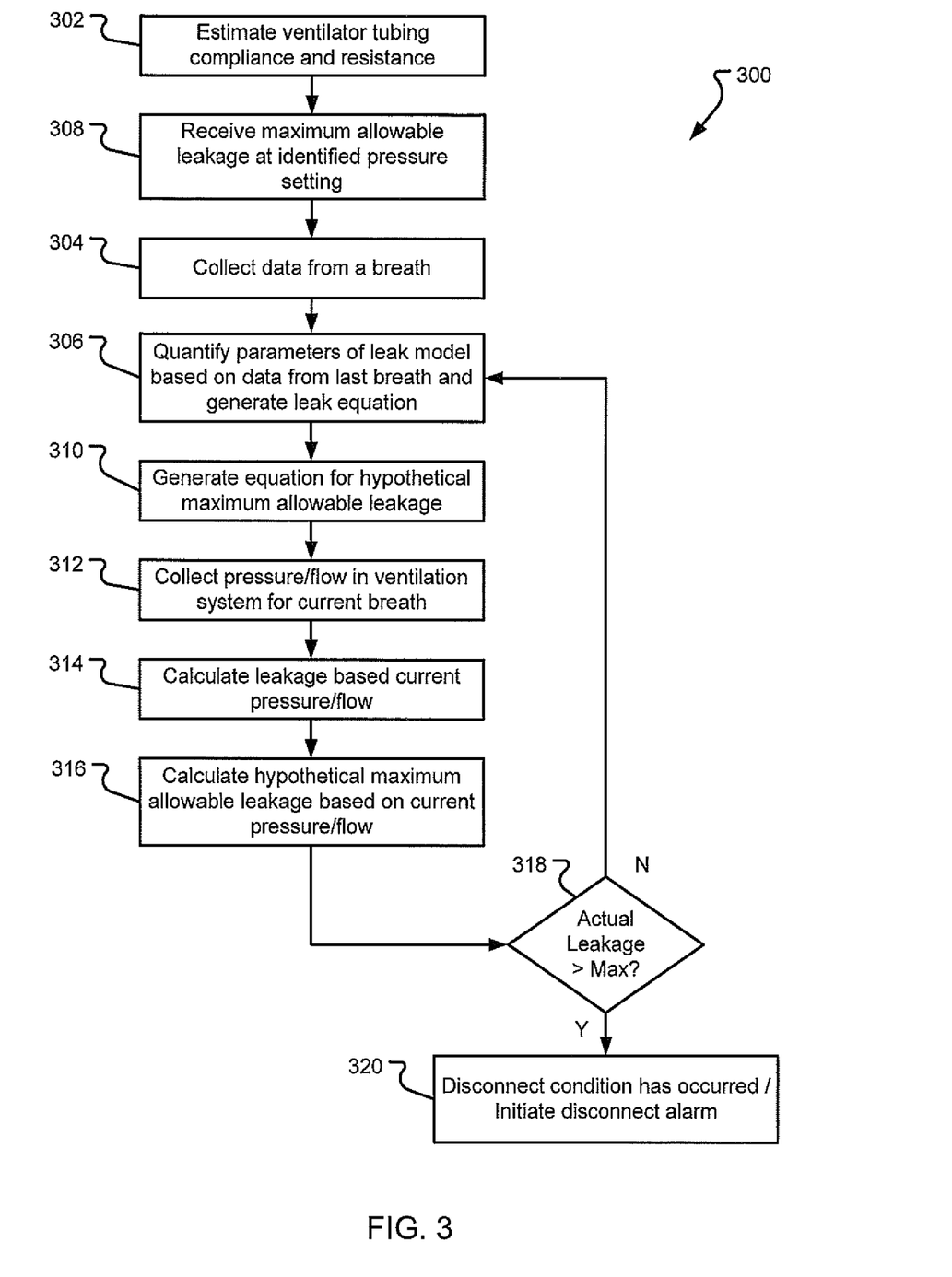
FIG. 3 illustrates an embodiment of a method of identifying when a disconnect condition has occurred during delivery of gas from a medical ventilator to a patient.

FIG. 3 illustrates an embodiment of a method of identifying when a disconnect condition has occurred during delivery of gas from a medical ventilator to a patient. In the method 300 shown, a medical ventilator such as that described above with reference to FIGS. 1 and 2 is used to provide ventilation to a patient.

In the method 300 illustrated, the ventilator system's compliance and resistance may be estimated in a compliance/resistance estimation operation 302. This is usually, but not necessarily, performed prior to connecting the ventilator to the patient (as previously described).

In the embodiment shown, a receive maximum leak operation 308 is also performed. In this operation 308 a maximum leak at a specified therapy condition such as a PEEP or other pressure level is obtained. The maximum leak received may be a selection of a maximum leak flow rate at a specified pressure. This information may be retrieved from memory after being received through the user interface from an operator of the ventilator, such as a nurse, doctor or other caregiver.

For example, in an embodiment when a caregiver initially sets up the ventilator to provide therapy to the patient, in addition to other selections such as selecting a PEEP value for the patient the caregiver may input a maximum allowed leak flow rate to be associated with a particular therapy. The leakage and PEEP value may be selected by the caregiver through interactions with the user interface such as via a drop down box, text box or by some other data input mechanism. In an embodiment, upon selection of a therapy type, the user interface may prompt the caregiver to accept a default maximum leakage or input a user-selected maximum leakage for the selected therapy.

After user selection, the selected maximum leakage and the particulars of the therapy may be stored and later obtained by the receive maximum leak operation 308. In an alternative embodiment, the receive maximum leak operation 308 may be considered to include the prompting for and receiving of the selected maximum leakage and the particulars of the therapy, as well as the storage of the information.

The receive maximum leak operation 308 may occur prior to connecting the patient to the ventilator or may occur after ventilation has begun. For example, a user may change the maximum leak during therapy, the new maximum leak being used in subsequent disconnection determinations.

In the method 300 illustrated, the ventilator is connected to the patient and operated for some initial period of time, e.g., for a breath, and data is obtained and stored in an initial data collection operation 304. While the data collection operation 304 may be performed prior to connection to the patient, it is also anticipated that the operation should be performed while the patient is receiving therapy from the ventilator so that leaks from the connection of the ventilation system to the patient may be characterized as well as the other leaks in the system.

The data obtained in the data collection operation 304 is then used to quantify the parameters of the leak model in the parameter quantification operation 306. In an embodiment, the parameter quantification operation 306 uses the data obtained in the data collection operation 304, e.g., the total leak volume during one breath cycle (inhalation and exhalation) and some or all of the pressure and flow data collected during the data collection operation 304. The data may be applied to a preselected mathematical formula in order to solve for parameters in the formula. In an embodiment, the mathematical formula is a leakage model that separates the leak into the sum of two leak components, inelastic leak and elastic leak, in which each component represents a different relationship between the quantity of leakage from the ventilation system and the measured current/instantaneous pressure and/or flow of gas in the ventilation system. As discussed above, the inelastic leak may be modeled as the flow through a rigid orifice of a fixed size while the elastic leak may be modeled as the flow through a different orifice of a size that changes based on the pressure (or flow) of the gas in the ventilation system.

In order to distinguish between the generic leak model used and the mathematical relationship (that contains the quantified parameters) from which leak volume may be solved for given data taken from the sensors on the ventilator, the terms "leak equation" and "leakage equation" will be used herein to generically refer to the latter. However, the reader will understand that, depending on the embodiment, the actual mathematical relationship may include multiple equations, formulae, or mathematical algorithms and quantified parameters and is not limited to a single equation.

An example of a method and system for modeling leak in a ventilation system to obtain a leak equation as a combination of an elastic leak component and an inelastic leak component can be found in commonly-assigned U.S. Provisional Patent Application Ser. No. 61/041,070, filed Mar. 31, 2008, titled VENTILATOR LEAK COMPENSATION, which application is hereby incorporated by reference herein. The VENTILATOR LEAK COMPENSATION represents one way of characterizing the leak from a ventilation system as a combination of elastic and inelastic components. Other methods and models are also possible and may be adapted for use with this technology.

As discussed above, a result of the parameter quantification operation 306 is a leak equation that, from one or more instantaneous measurements of pressure and/or flow in the ventilation system, can be used to calculate an estimate of the resulting instantaneous and total leakage from the ventilation system. Thus, given the leak equation, pressure and/or flow data can be monitored during therapy and the instantaneous leak and total leak from the ventilation system can be calculated. The resulting leak value estimates will take into account both elastic leak and the inelastic leak.

In an embodiment, the data collection operation 304 and the parameter quantification operation 306 may be performed as a single operation or as separate operations. In an embodiment, the operations 304 and 306 may be repeated periodically, based on time or breathing cycles, in order to obtain accurate estimates.

For example, in an embodiment, the data collection operation 304 may obtain data from a particular breath of a patient. This data may then be used in the parameter quantification operation 306 to solve for the parameters in the leak model and generate the leakage equation for use in calculating the instantaneous leak in a subsequent breath. In an embodiment, the data collection operation 304 and the leak model parameter quantification operation 306 are repeated at the end of each breath so that the instantaneous leak is estimated using an equation derived from data taken during the immediately previous breath.

The maximum leakage and the particulars of the therapy selected by and received from the caregiver are used to generate a maximum allowable leakage equation in a second equation generation operation 310. In this operation 310, a maximum leakage equation is created using the selected maximum leakage and the particulars of the therapy (e.g., PEEP value). In an embodiment, the same mathematical model as used to generate the actual leakage equation is used to generate the maximum leakage equation. As with the actual leakage equation, the maximum leakage equation is a mathematical relationship that, when provided instantaneous pressure and/or flow measurements can be used to solve for a leak value, albeit in this case the leak value is the hypothetical maximum allowable leakage for that instantaneous measurement or set of measurements.

The maximum allowable leak equation generation operation 310 may be repeated for every breath as shown or, in an alternative embodiment, performed only upon receipt of a new maximum allowable leakage in the receive maximum allowable leakage operation 308.

During therapy the ventilator monitors the pressure and/or flow in the ventilator system, illustrated in FIG. 3 and sampling operation 312. In an embodiment, the sampling operation 312 includes periodically (e.g., every 5 milliseconds, 10 milliseconds, 25 milliseconds, etc.) obtaining pressure and/or flow measurements from one or more locations within the ventilation system over the period of a single breath by the patient. In an alternative embodiment, the sampling operation 312 may collect data for less than a single breath or more than a single breath before the method 300 proceeds to the following operations as shown.

Depending upon the form or format of data required by a particular equation, the sampling operation 312 may also include making one or more calculations based on the data obtained during the sampling operation 312. For example, if pressure data is obtained in the form of an analog or digital signal, the signal may need to be converted into a pressure value in the correct unit of measure (pounds per square inch, bars, millimeters of mercury, etc.). In another embodiment, an equation may require a measurement from a specific location in the ventilation system such as at the patient interface even though the ventilation system may not have a sensor at that location in the ventilation system. Thus, data from a sensor or sensors located elsewhere in the system (or data from a different type of sensor at the location) may be mathematically manipulated in order to obtain an estimate for the value at the necessary location.

In the method 300 as shown, after the sampling operation 312 has obtained the current pressure and/or flow measurements for the breath, the instantaneous actual leakage for the sampling period (e.g., for the just-ended breath) is calculated in an instantaneous leak calculation operation 314. The operation 314 uses the actual leakage equation generated in the leak equation generation operation 306 and the current pressure and/or flow measurements. In an embodiment in which the equation characterizes both the elastic and inelastic leak components, the calculated leak represents the total leak due to the combination of both leak components. In an alternative embodiment, the total leak for the breath may be calculated using flow data (e.g., by determining the net flow for the breath) rather than by using the actual leak equation to determine the total leakage for the breath.

In addition to the leak calculation operation 314 the method 300 also performs a maximum allowable leak calculation 316. In the maximum allowable leak calculation 316, the maximum leakage equation and the current pressure and/or flow measurements are used to calculate the maximum allowable leakage for the appropriate period (e.g., a single breath as illustrated or multiple breaths). In an embodiment in which the equation characterizes both the elastic and inelastic leak components, the calculated maximum leak represents the total maximum allowable leak volume due to the combination of both leak components.

In the method 300, the ventilator then compares the calculated maximum allowable leakage and the actual leakage in a determination operation 318. In the embodiment shown, this determination is performed at the end of a breath cycle. The maximum allowable leak for the entire breath cycle is calculated and compared to the calculated actual leak for the same breath cycle. If the determination operation 318 determines that the maximum allowable leakage has not been exceeded by the actual leakage for the breath, then the ventilation system is considered to still be connected to the patient and the method 300 returns to the parameter quantification operation 306 so that the analysis may be performed again for the next breath using the most recent data. Note that the data collected in the sampling operation 312 can then be used in place of the data collected in the initial data collection operation 304 to revise the parameters of the leak model and obtain new a leak equation. In an embodiment, the parameter quantification operation 306 may then be performed using the data from the last breath. In an alternative embodiment, the disconnect determination may be performed at set intervals different from the normal data acquisition sampling period, e.g., every 50 milliseconds, every 5 breaths, or at a specific point or points in the patient's breathing cycle. Additional conditions may be combined with the maximum allowable leak threshold to account for idiosyncrasies of specific platforms and operating conditions.

If the determination operation 318 determines that the actual leakage exceeds the maximum allowed leakage calculated based on measurements taken during the same period, then the ventilation system is considered to have become disconnected from the patient.

Upon determination that there has been a disconnection, a disconnect condition operation 320 is performed. This operation 320 may include initiating an alarm to alert caregivers of the condition. In addition, the ventilator may initiate a patient reconnection detection procedure to determine when normal ventilation may resume. Such a reconnect procedure may include delaying for a period of time and then delivery of a certain flow rate and checking for acceptable flow return through the system, and/or interrupting drug or therapy delivery by ancillary equipment under the control of the ventilator. Other actions may also be performed upon detection of a disconnect condition such as the logging of different or additional data, transmission of notifications to remote locations and the opening and/or closing of valves in the ventilation system to modify the flow path of gas. Although not shown, in an embodiment after a disconnect has been deemed detected by the method 300, some or all of the method 300 may be repeated for a period of time.

Figure 4:
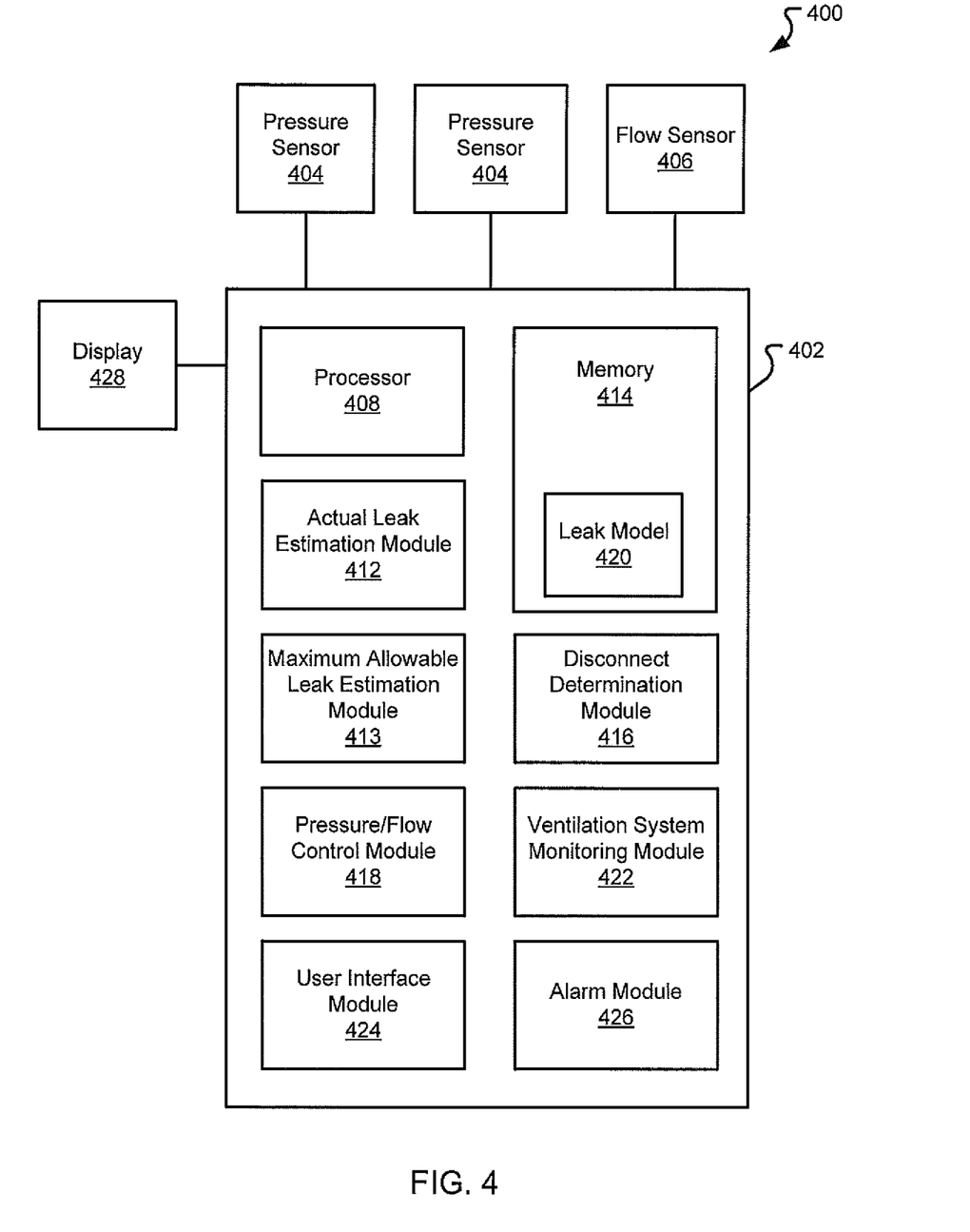
FIG. 4 illustrates a functional block diagram of modules and other components that may be used in an embodiment of ventilator that both compensates for leaks and detects disconnect conditions.

FIG. 4 illustrates a functional block diagram of modules and other components that may be used in an embodiment of a leak-compensating ventilator that detects disconnects. In the embodiment shown, the ventilator 400 includes pressure sensors 404 (two are shown placed at different locations in the ventilator system), flow sensors 406 (one is shown), and a ventilator control system 402. The ventilator control system 402 controls the operation of the ventilator and includes a plurality of modules described by their function. In the embodiment shown, the ventilator control system 402 includes a processor 408, memory 414 which may include mass storage as described above, an actual leak estimation module 412, an maximum allowable leak estimation module 413, a disconnect determination module 416, a pressure and flow control module 418, a monitoring module 422, a leak model 420, a user interface module 424, an alarm module 426, and a display 428. The processor 408 and memory 414 have been discussed above. Each of the other modules will be discussed in turn below.

The main functions of the ventilator such as receiving and interpreting operator inputs and changing pressure and flow of gas in the ventilator circuit are performed by the control module 418. In the context of the methods and systems described herein, the module 418 will perform one or more actions upon the determination that a patient receiving therapy has become disconnected from the ventilation system. The actions performed upon detection of disconnect may be different depending upon the current therapy mode of the ventilator 400.

The disconnect determination module 416 identifies when the ventilator system is disconnected from the patient. This is performed by comparing an actual leakage of the ventilator system to a maximum allowable leakage. The comparison may be performed at the end of each breath, or over the span of multiple breaths in some embodiments, at which time the calculated actual leakage for the breath is compared to the maximum allowable leakage for the chosen breath interval. If the actual leakage exceeds the maximum allowable leakage, then a disconnect condition has occurred. The disconnect condition is then indicated to the alarm module 426 so that one or more alarms and/or notifications can be initiated to indicate the disconnect condition to caregivers.

The actual leakage of the ventilator is calculated by the actual leak estimation module 412 and made available to the disconnect determination module 416 so that it can perform its analysis. In an embodiment, the actual leakage is determined based on a predetermined actual leak equation and current data concerning the pressure and/or flow in the ventilator system. In an embodiment, the actual leakage is calculated every 5 milliseconds based on a new pressure measurement obtained at the same interval. In an alternative embodiment, the actual leakage may be calculated less often and may be calculated based on an average of multiple pressure and/or flow measurements taken over multiple sampling periods.

In an embodiment, the actual leak equation is generated by the actual leak estimation module 412, the pressure/flow control module 418 or another module (not shown) dedicated to the purpose of developing actual leak equation. As discussed above, although referred to as an equation, the actual leak equation may include multiple mathematical equations, formulae and/or correlations from which, given instantaneous pressure and/or flow measurements from the ventilation system, an actual leakage for the ventilation system may be calculated.

The actual leak equation is generated from one or more mathematical models 420 stored in memory 414. The leak model 420 uses pressure and/or flow observed in the ventilation system over regular periods of respiratory cycles (inhalation and exhalation) and apply physical and mathematical principles derived from mass balance and characteristic waveform settings of ventilation modalities (regulated pressure or flow trajectories) to derive the parameters of the leak model incorporating both rigid and elastic (variable pressure-dependent) orifices. In an embodiment, the mathematical model may be a model such as:

$$Q_{inelastic} = R_1 * P_i^x$$

$$Q_{elastic} = R_2 * P_i^y$$

wherein $Q_{elastic}$ is the instantaneous leak flow due to elastic leaks in the ventilation system, $Q_{inelastic}$ is the instantaneous leak flow due to inelastic leaks in the ventilation system, $R_1$ is the inelastic leak constant, $R_2$ is the elastic leak constant, $P_i$ is the current or instantaneous pressure measurement, x is an exponent for use when determining the inelastic leak and y is an exponent different than x for use when determining the elastic leak. The group $R_1 * P_i^x$ represents flow through an orifice of fixed size as a function of instantaneous pressure $P_i$ and the group $R_2 * P_i^y$ represents flow through a different orifice that varies in size based on the instantaneous pressure. The models above presuppose that there will always be an elastic component and an inelastic component of leakage from the ventilation system. In the absence of an elastic component or a leak source of varying size, $R_2$ would turn out be zero.

In the embodiment shown, the actual leakage equation may be determined by taking data over multiple sampling periods (such as over a single breath), estimating the leakage during the same period from flow measurements and solving the above models for the leak constants $R_1$ and $R_2$ using the pressure measurements from the same period. Given pressure data taken during a breath, the actual leakage equation may be integrated over the breath to obtain a calculated actual leakage (as a volume of gas leaked during the breath).

Likewise, the maximum allowable leakage of the ventilator is calculated by the maximum allowable leak estimation module 412 and made available to the disconnect determination module 416 so that it can perform its analysis. In an embodiment, the maximum allowable is determined based on a predetermined maximum allowable leak equation and current data for the pressure and/or flow in the ventilator system. In an embodiment, the maximum allowable leakage is calculated at the same time the actual leakage is calculated and using the same data as used by the actual leakage.

The maximum allowable leak equation is determined based on an operator-selected maximum allowable leakage at specified PEEP value or other therapy condition indicative of a pressure. In one embodiment based on the above leak model, R2 may be assumed constant as it is related to elastic properties of the tubing and interface. Then, the current R2 and the given maximum leak flow rate at PEEP may be inserted into the combined leak model equations (elastic leak rate+inelastic leak rate=maximum allowable leak rate) to compute a R1 value corresponding to maximum leak rate allowed. Therefore, given the two data points, in an embodiment the same model 420 used to determine the actual leakage equation is solved using the operator-selected data to generate the maximum allowable leak equation. In an alternative embodiment, a model different from that used to determine the actual leak equation may be used. In an embodiment, the actual leak equation is generated by the maximum allowable leak estimation module 413, the pressure/flow control module 418 or another module (not shown) dedicated to the purpose of developing actual leak equation. Given pressure data taken during a breath, the maximum allowable leakage equation may be integrated over the breath to obtain a calculated maximum allowable leakage (as a volume of gas leaked during the breath) that takes into account the inelastic properties of the leaks from the system as well as the different pressures observed throughout the breath.

The current conditions in the ventilation system are monitored by the monitoring module 422. This module 422 collects the data generated by the sensors 404, 406 and may also perform certain calculations on the data to make the data more readily usable by other modules. In an embodiment, the monitoring module 422 receives data and provides it to each of the other modules in the ventilator control system 402 that need the current pressure or flow data for the system.

The user interface module 424 is provided to receive the operator selections through the display 428 of the maximum allowable leak and an associated therapy condition or setting (such as PEEP value).

The system 400 illustrated will compensate the disconnect determination for allowable leaks due to elastic and inelastic leaks in the ventilation system. By compensating for the inelastic as well as the elastic components of dynamic leaks, the medical ventilator can more accurately and precisely identify the disconnect condition while allowing acceptable levels of leak.

Figure 5:
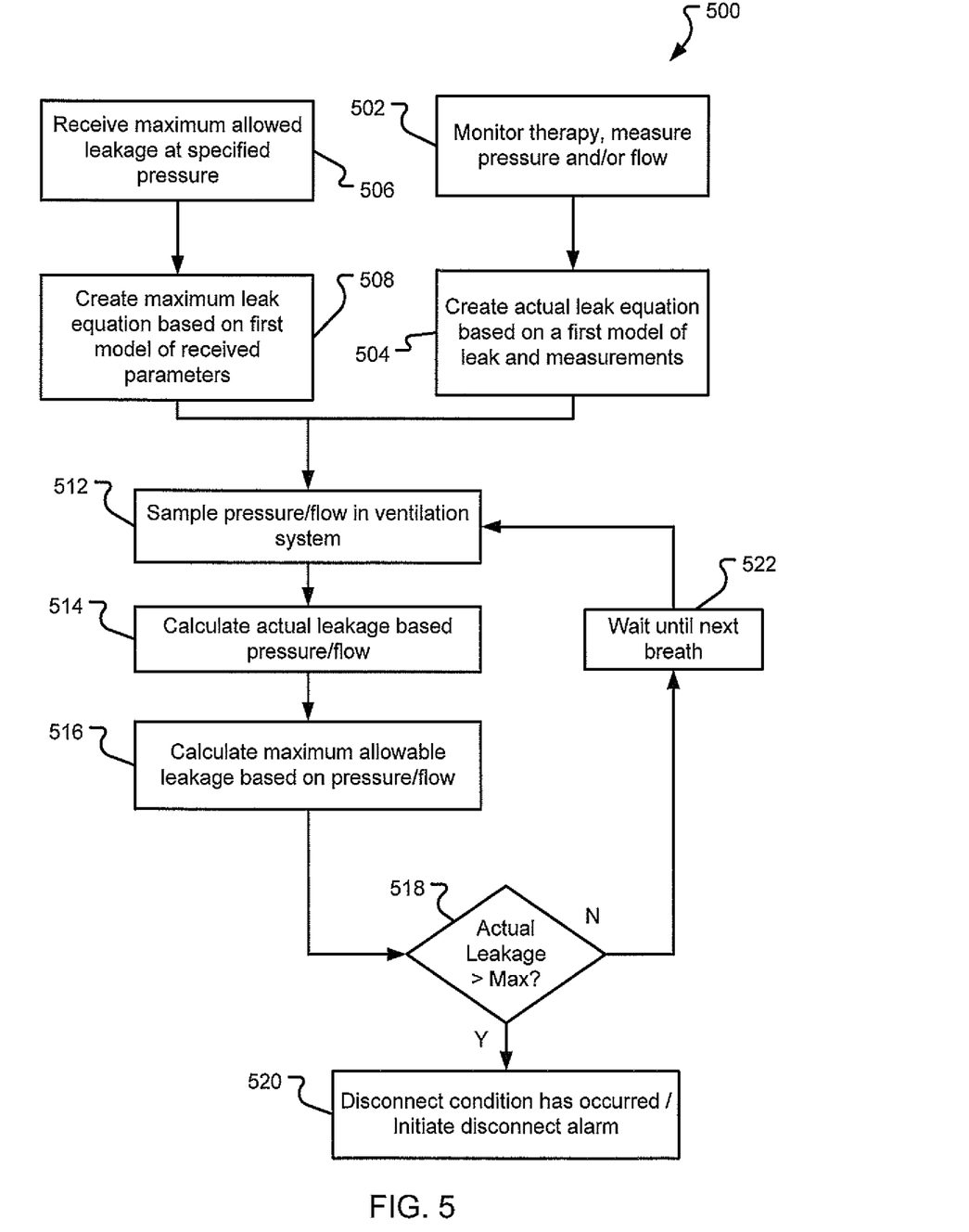
FIG. 5 illustrates an embodiment of a method of detecting disconnection of a ventilation system during delivery of gas from a medical ventilator.

FIG. 5 illustrates another embodiment of a method for detecting a disconnect in ventilator. In the method 500 shown, pressure and/or flow is monitored by the ventilator while providing therapy in an initial monitoring operation 502. Then as described above with reference to FIG. 3, using the data obtained during the initial monitoring operation 502 the actual leak equation is generated for use in determining the actual leakage for a subsequent breath 504.

Independently from the initial monitoring operation 502, an operator may provide a maximum allowable leakage to the ventilator, which command and associated information is received in a receive maximum allowable leakage operation 506. In response to receiving the command and maximum allowable leakage information, the ventilator generates a maximum leak equation in a generate maximum allowable leak equation operation 508, as described with reference to FIG. 3.

The remaining operations of sampling the pressure and/or for a breath 512, calculating actual leakage for the breath 514, calculating maximum allowable leakage for the breath 516, and determining if the actual leakage exceeds the maximum leakage 518 (and initiating a disconnection operation 520 if disconnect is detected) proceed as described in FIG. 3. This includes repeating the analysis every sample period (as illustrated by the waiting operation 522) until such time as a disconnect condition is determined.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples. For example, the operations and steps of the embodiments of methods described herein may be combined or the sequence of the operations may be changed while still achieving the goals of the technology. In addition, specific functions and/or actions may also be allocated in such as a way as to be performed by a different module or method step without deviating from the overall disclosure. In other words, functional elements being performed by a single or multiple components, in various combinations of hardware and software, and individual functions can be distributed among software applications. In this regard, any number of the features of the different embodiments described herein may be combined into one single embodiment and alternate embodiments having fewer than or more than all of the features herein described are possible.

While various embodiments have been described for purposes of this disclosure, various changes and modifications may be made which are well within the scope of the present invention. For example, the systems and methods described herein could be adapted to instantaneous determine a disconnect condition based very small sampling periods. Numerous other changes may be made which will readily suggest themselves to those skilled in the art and which are encompassed in the spirit of the disclosure and as defined in the appended claims.

What is claimed is:

1. A method of detecting disconnection of a ventilation system during delivery of gas from a medical ventilator to a patient, the ventilation system comprising a processor and a memory, the method comprising:
   developing, by the ventilation system, an actual leakage equation describing leakage from the ventilation system as a function of pressure in the ventilation system, wherein developing the actual leakage equation comprises:
      taking one or more measurements of instantaneous pressure or instantaneous flow in the ventilation system during a period of delivery of gas to the patient;
      determining an actual leakage from the ventilation system during the period;
      based on the one or more measurements and the actual leakage for the period, modeling the actual leakage as a first leakage component through a first orifice of a fixed size and a second leakage component through a second orifice of a varying size, wherein the first and second leakage components are different functions of pressure in the ventilation system; and
      developing the actual leakage equation based on the first and second leakage components;
   developing a maximum leakage equation describing a maximum allowed leakage from the ventilation system as a function of pressure in the ventilation system;
   monitoring pressure in the ventilation system during delivery of gas to the patient during a breath;
   calculating an actual breath leakage from the ventilation system during the breath based on a current pressure using the actual leakage equation;
   calculating a maximum allowed leakage from the ventilation system during the breath based on the current pressure using the maximum leakage equation; and
   comparing the calculated maximum allowed leakage and the actual breath leakage.

2. The method of claim 1 further comprising:
   identifying that the ventilation system has been disconnected from the patient based on results of the comparing operation.

3. The method of claim 1 further comprising:
   calculating the actual leakage from the ventilation system based on the monitored pressure, the first leakage component and the second leakage component.

4. The method of claim 1 wherein developing a maximum leakage equation further comprises:
   receiving a maximum allowed leak flow at a selected therapy setting; and
   developing the maximum leakage equation based on the maximum allowed leak flow and the selected therapy setting.

5. The method of claim 4 wherein developing a maximum leakage equation further comprises:
   based on the maximum allowed leakage value and selected therapy setting, modeling the maximum leakage as a third leakage component through a third orifice of a fixed size and a fourth leakage component through a fourth orifice of a varying size, wherein the third and fourth leakages are different functions of pressure in the ventilation system; and
   developing the maximum leakage equation based on the third and fourth leakage components.

6. The method of claim 5 further comprising:
   calculating the maximum leakage from the ventilation system based on the current pressure, the third leakage component and the fourth leakage component.

7. The method of claim 4 further comprising:
   receiving the maximum allowed leak flow value and the selected therapy setting from an operator of the ventilator.

8. The method of claim 4 further comprising:
   identifying a pressure value associated with the selected therapy setting.

9. The method of claim 4 wherein the selected therapy setting is an operator-selected positive end expiratory pressure.

10. The method of claim 2 wherein identifying further comprises:
   initiating a disconnect alarm.

11. A method of detecting disconnection of a ventilation system during delivery of therapy to a patient, the ventilation system comprising a processor and a memory, the method comprising:
   generating, by the ventilation system, an actual leak equation based on a leak model and measurements taken during the delivery of therapy to the patient, wherein the leak model models leakage from the ventilator circuit as a first leakage component through a first orifice of a fixed size and a second leakage component through a second orifice of a varying size, wherein the first and second leakage components are different functions of pressure in the ventilation system;
   generating a maximum leak equation based on the leak model, and a maximum allowed leakage at a specified pressure;
   measuring pressure in the ventilation system during a current therapy period; and
   calculating an actual leak from the ventilation system for the current therapy period based on the pressure using the actual leak equation;

calculating a maximum allowable leak from the ventilation system for the current therapy period based on the pressure using the maximum leak equation; and selecting, based on a comparison of the actual leak and the maximum allowable leak, one of at least two ventilator connection states.

12. The method of claim 11 wherein selecting further comprises:

selecting a second state indicating that the patient is connected to the ventilation system.

13. The method of claim 11 wherein selecting further comprises:

selecting a first state indicating that the patient is disconnected from the ventilation system.

14. The method of claim 13 further comprising:

initiating a disconnect alarm.

15. The method of claim 11 wherein generating an actual leak equation further comprises:

monitoring pressure and flow in the ventilation system during a previous therapy period different from the current therapy period;

estimating the leakage from the ventilation system during the previous therapy period based on the measured flow;

generating the actual leak equation based on the leak model, the pressure for the previous therapy period and the estimated leakage for the previous therapy period.

* * * * *